US005626853A

United States Patent [19]

Bara et al.

[11] Patent Number: 5,626,853

[45] Date of Patent: May 6, 1997

[54] AQUEOUS MAKE-UP GEL CONTAINING ORGANOPOLYSILOXANE

[75] Inventors: Isabelle Bara, Paris; Myriam Mellul, L'Hay-les-Roses, both of France

[73] Assignee: L'Oreal, Paris, France

[21] Appl. No.: 403,398

[22] Filed: Mar. 14, 1995

[30] Foreign Application Priority Data

Mar. 14, 1994 [FR] France .................................... 94 02944

[51] Int. Cl.$^{6}$ ........................................................ A61K 6/00

[52] U.S. Cl. .................. 424/401; 424/78.03; 424/78.08; 424/78.31

[58] Field of Search ................................ 424/401, 78.03, 424/78.08, 78.31

[56] References Cited

U.S. PATENT DOCUMENTS

| | | | |
|---|---|---|---|
| 4,759,924 | 7/1988 | Luebbe et al. | 424/42 |
| 5,080,828 | 1/1992 | Terae | 252/358 |
| 5,266,321 | 11/1993 | Shukuzaki et al. | 424/401 |
| 5,304,334 | 4/1994 | Lahanas et al. | 252/314 |
| 5,415,860 | 5/1995 | Beucherie et al. | 424/401 |

FOREIGN PATENT DOCUMENTS

| | | |
|---|---|---|
| 0540357 | 5/1993 | European Pat. Off. . |
| 2686510 | 7/1993 | France . |
| WO92/09263 | 6/1992 | WIPO . |

*Primary Examiner*—Mark D. Sweet
*Attorney, Agent, or Firm*—Finnegan, Henderson, Farabow, Garrett & Dunner, L.L.P.

[57] ABSTRACT

The invention relates to a gel containing an aqueous phase, a hydrophilic polymer as a gelling agent, a colouring material which is soluble or dispersible in the aqueous phase and at least one organopolysiloxane solubilized in the aqueous phase. This gel is usable in the cosmetics field for making up both the face and the human body.

19 Claims, No Drawings

AQUEOUS MAKE-UP GEL CONTAINING ORGANOPOLYSILOXANE

The invention relates to an aqueous gel containing organopolysiloxane, which is usable in the cosmetics field for making up the face and/or body. The gel takes the form, in particular, of a make-up foundation or a blusher. The invention also relates to a make-up process which consists of applying this gel to the face.

Aqueous gels comprising hydrophilic phase containing gelling agents essentially composed of hydrophilic polymers are sometimes used for making up the skin; these aqueous gels do not contain a fatty phase. They can, in addition, be coloured by the incorporation of hydrophilic pigments and/or colorants and appear opaque or translucent. These gels are used especially in the preparation of make-up foundations, blushers or eyeshadows. These translucent coloured aqueous gels are known for their capacity to impact an appearance of particularly good health, and for their coolness on application; the user of such gels does not have the feeling of actually wearing make-up.

These traditional gels have the drawback of making individuals having dry skin feel uncomfortable on account of the absence of fats, and of producing an effect of stickiness and tautness of the skin as a result of the presence of gelling agents. In addition, the application of these gels is often difficult as a result of a lack of slipperiness and an excessively rapid drying; these gels endow the skin with a heterogeneity of make-up, that is to say, with light and dark areas.

To remedy the discomfort associated with these gels, one solution is to incorporate hydrating agents such as, for example, polyols, e.g., glycerol, in the gels, but the effect of stickiness imparted to the skin then becomes enhanced. Hence these drawbacks make the use of these gels difficult or may even preclude their use.

There thus remains the need for a make-up gel which is easy to apply, which glides and spreads well, is non-sticky, which does not dry too quickly and which endows the skin with a homogeneous make-up. The inventors have now found a fluid aqueous make-up gel that enables these objectives to be achieved.

According to the invention, this aqueous gel contains an aqueous phase, at least one hydrophilic polymer as a gelling agent, and a colouring material which is dispersible or soluble in the aqueous phase, and further comprises, in addition, at least one organopolysiloxane solubilized in the aqueous phase.

Aqueous skin care gels containing glycerol as water-soluble humectant, a hydrophilic gelling polymer and a mixture of silicone gum in a liquid silicone in the form of a macro-dispersion are disclosed in the document WO 92/09,263. However, these gels are cloudy as a result of the heterogeneous and macroscopic dispersion of gum and liquid silicone. The oily globules dispersed in the gel have an average diameter of several µm. Further, this gel, which remains stable as a result of its high viscosity, i.e., on the order of 4–300 Pa.S (40 to 3000 poises), breaks when applied to the skin, releasing "bags of oil". The outcome is a heterogeneous appearance which is immediately visible, and this is not without some attendant problems in the case where the use of the product for make-up is contemplated.

In contrast, the gel according to the invention is entirely suitable for make-up. It can endow the skin with a very natural appearance, and one of particularly good health, a non-greasy appearance and a non-stick feel. It can be applied readily to the skin without becoming fluffy; it can glide well and not dry too rapidly. The resulting make-up can be perfectly homogeneous. The cosmetic properties of the gel according to the invention are hence superior to those of traditional gels.

These numerous advantages make the gel of the invention appropriate for making up any type of skin, and even dry skins.

The content of organopolysiloxane solubilized in the aqueous gel of the invention preferably ranges from 0.02% to 50% by weight relative to the total weight of the gel, depending on the type of organopolysiloxane used. Above 50% of organopolysiloxane, the composition endows the skin with a sticky appearance.

The organopolysiloxanes which are usable in the invention may be rendered soluble either by chemical modification, or physically by the addition of a compound such as a surfactant. They may be used alone or mixed. In particular, as a chemically solubilized organopolysiloxane, a copolymer of siloxane and hydrolysed or unhydrolysed protein, as described, in particular, in the document EP-A-540,357, the disclosure of which is hereby incorporated by reference, may be used. Examples of such copolymers are the copolymers of polysiloxane or derivatives linked covalently by grafting to a protein, hydrolysed or unhydrolysed, such as casein, elastin, collagen, keratin, silk or a wheat or soya protein.

It is possible, for example, to use a phosphated siloxane grafted on to a hydrolysed wheat protein. These grafted copolymers are sold, in particular, by the company CRODA under the name Crodasone W, by the company PHOENIX under the name Pecosil SWP 83 or the name Non-P-Silicon Protein.

The copolymers of siloxane and hydrolysed or unhydrolysed protein are preferably present in an amount of 1% to 50%, and still more preferably from 10% to 50%, by weight relative to the total weight of the gel.

As another chemically solubilized organopolysiloxane which is usable in the gel of the invention, dimethicone copolyols (CTFA nomenclature) and their derivatives may also be mentioned. Dimethicone copolyols have, in particular, been put forward by the company DOW CORNING at the 17th International Congress of the I.F.S.C.C. in October 1992, and reported in the publication "Water-soluble dimethicone copolyol waxes for personal card industry" by Linda Madore et al., pages 1 to 3.

These dimethicone copolyols are water-soluble polydimethylsiloxanes (PDMS) containing one or more ether functions (oxyalkylene, in particular oxyethylene and/or oxypropylene). Such dimethicone copolyols are sold, in particular, by the company GOLDSCHMIDT under the name ABIL B8851 or ABIL B88183. The compounds KP 351 to 354 and KP 615 A sold by the company SHIN ETSU or DMC 6038 of the company WACKER may also be mentioned.

The dimethicone copolyol derivatives which are usable in the invention are, in particular, dimethicone copolyols containing a phosphate, sulphate, myristamidopropyldimethylammonium chloride, stearate, amine, glyco-modified, and the like, group.

As dimethicone copolyol derivatives, the compounds sold by the company SILTECH under the name Silphos A100, Siltech amine 65, Silwax WDIS, myristamido silicone quat, or by the company PHOENIX under the name Pecosil PS 100, are used in particular. It is also possible to use the derivatives sold by the company WACKER under the name VP 1661, or by the company DOW CORNING under the name 2501 cosmetic wax.

The dimethicone copolyols and their derivatives are used in the composition according to the invention at concentrations preferably from 0.5% to 20% by weight relative to the total weight of the gel.

As a physically solubilized organopolysiloxane which is usable in the invention, organopolysiloxanes solubilized using a surfactant of HLB value above 8, and preferably of not less than 10, may be mentioned. As is well known, HLB (hydrophilic-lipophilic balance) is understood to mean the balance between the size and strength of the hydrophilic group and the size and strength of the lipophilic group of the surfactant. These organopolysiloxanes take the form of an emulsion or microemulsion containing from 10% to 90% by weight of organopolysiloxane relative to the total weight of the emulsion or microemulsion.

According to the invention, the average size of the dispersed particles of organopolysiloxane is the order of 1 μm, enabling a very homogeneous make-up of the skin to be obtained.

Preferably, these organopolysiloxanes can be polydimethylsiloxanes (PDMS) which are optionally of the gum type, alone or mixed with cyclomethicones. These physically solubilized organopolysiloxanes are present in an amount preferably from 0.02% to 20% by weight relative to the total weight of the gel; even at an organopolysiloxane content of greater than 10% by weight, the make-up gel of the invention remains stable, which is not the case with the gel which is the subject of the document WO-92/09,263, referred to above.

Examples of physically solubilized organopolysiloxanes which are usable in the invention are, in particular, SM2140 or SM2112 of DOW CORNING, MFF 5015-70 of SILTECH, TP 503 or TP 233 B of UNION CARBIDE.

The surfactants of HLB (hydrophilic-lipophilic balance) value above 8 are, in particular, ethers of a $C_6$ to $C_{24}$ fatty alcohol and poly(ethylene oxide). They are incorporated, in general, in the proportion of 0.5% to 30% by weight relative to the total weight of the emulsion or microemulsion. They are, for example, polyoxyethylene (12) cetyl/stearyl ether or polyoxyethylene (20) cethyl/stearyl ether.

The gel according to the invention has a soft or fluid consistency. Its absolute viscosity, measured at 25° C. using a EBBRECHT viscometer, has a value from 1 poise to 100 poises (0.1 Pa.s to 10 Pa.s), and preferably a value of 5 poises to 30 poises (0.5 Pa.s to 3 Pa.s).

It is altogether surprising that, with viscosity values as low as 1 poise (0.1 Pa.s), organopolysiloxanes can be incorporated in this gel at contents of greater than 10% by weight relative to the total weight of the gel.

The viscosity of the gel of the invention depends on the nature and amount of the hydrophilic polymer or polymers used as gelling agents. These gelling agents are, for example, acrylic and polymethacrylic polymers of copolymers such as acrylic acid/ethyl acrylate copolymers and carboxyvinyl polymers. Examples of such polymers or copolymers are, in particular, the "carbomers" (CTFA) sold by the company GOODRICH under the name Carbopol, or the polyglyceryl methacrylate sold by the company GUARDIAN under the name Lubragel, or alternatively the polyglyceryl acrylate sold under the name Hispagel by the company HISPANO CHIMICA, or lastly the polyacrylamide/$C_{13}$–$C_{14}$ isoparaffin/laureth-7 mixture sold by the company SEPPIC under the name Sepigel.

As other gelling agents which are usable in the invention, there may be mentioned: polysaccharide derivatives, for instance cellulose derivatives such as carboxymethylcellulose, hydroxymethylcellulose, hydroxypropylcellulose, microcrystalline cellulose; xanthan, gellan and rhamsan polymers, alginates, maltodextrin, starch and its derivatives, hyaluronic acid and its salts, gum karaya, carob flour and guar derivatives, in particular hydroxypropylguar. It is also possible to use as hydrophilic polymer polyethylene glycols (PEG) and their derivatives, polyvinylpyrrolidones and their derivatives.

Preferably, an acrylic derivative such as a carbomer (Carbopol), which is neutralized in the traditional manner using a basic agent such as, for example, triethanolamine or sodium hydroxide, a polyglyceryl methacrylate (Lubragel) or polysaccharides such as cellulose derivatives is/are used as hydrophilic polymer.

These hydrophilic polymers are generally present in the amount of 0.01% to 30%, and preferably 0.1% to 5%, by weight relative to the total weight of the gel.

As colouring materials, the gel of the invention can contain organic colorants and/or contain pigments, which are preferably hydrophilic or rendered hydrophilic in order to effect their dispersion in the medium.

As hydrophilic organic colorants, there may be mentioned water-soluble salts such as Ponceau disodium salt, alizarin green disodium salt, guinoline yellow, amaranth trisodium salt, tartrazine disodium salt, rhodamine monosodium salt, resorcin monosodium salt, quinizarin greens, pyramine trisodium salt, fuchsin disodium salt, betanin, xanthophyll and caramel. When the make-up gel comprises only these colorants, it has a transparent and somewhat translucent appearance.

As pigments which are hydrophilic or rendered hydrophilic, water-dispersible pigments are used, such as, in particular, metal oxides whose average particle size is optionally in the nanometer range. These metal oxides are, for example, iron, titanium, manganese, zinc and chromium oxides.

As another pigment which is dispersible in the aqueous phase of the gel of the invention, there may be mentioned the melanin pigment of particle size less than 1 μm, and more especially less than 500 nm, prepared according to the process described in French Patent Application 93/04960, the disclosure of which is hereby incorporated by reference.

According to this process, melanin of natural or synthetic origin is, in a first step, solubilized at a temperature of between 10° C. and 50° C. in an aqueous solution containing an alkalinizing agent such as, for example, sodium hydroxide and/or a sequestering agent such as, in particular, ethylenediaminetetra(methylenephosphonic acid) sodium salt, and then, in a second step, the melanin is precipitated by adding an alkaline-earth metal salt. The precipitate of melanin pigment thereby obtained is then isolated, for example by filtration, before being lyophilized.

As a melanin pigment of synthetic origin, it is possible to use the melanin pigment obtained in a known manner by oxidizing 5,6-dihydroxyindole. The melanin pigment, when present in the gel, is preferably combined with metal oxides such as those described above, especially in the preparation of make-up foundations.

When the gel contains pigments, it has an opaque appearance. The colorants or pigments are generally present in an amount of 0.001% to 10% by weight relative to the total weight of the gel and preferably 0.01% to 1% for the colorants and 1% to 10% for the pigment.

According to the invention, it is, in addition, possible to add additives to the gel, such as those additives traditionally used in the cosmetics field. The additive can be present in the amount of 0–30% by weight relative to the total weight of the gel. The exact amounts are dependent on the type of additive chosen, and their determination in within the competence of a person skilled in the art.

This additive can be a gelling agent other than a polymer, and, for example, a hydrophilic silica or a silicate such as aluminum magnesium silicate belonging to the montmorillonite group, such as hectorites and bentonites. The additive can also be a water-soluble active agent such as, in particular, a polyol (glycerol, propylene glycol, butylene glycol) for its hydrating properties. Contrary to the aqueous gels of the prior art, the sensory properties of the aqueous gel of the invention are in no way impaired by the presence of polyol; it may be used in the amount of 0.5% to 20% by weight relative to the total weight of the gel.

Other water-soluble hydrating active agents may also be incorporated in the gel of the invention, for example, chondroitin sulphates, chitin derivatives, hyaluronic acid, protein, in particular keratin, derivatives, various monohydric alcohols (ethanol, isopropanol) for the purpose of imparting more coolness to the gel when it is spread, and also sugars such as sorbitol, glucose and sucrose; trace elements, amino acids, vitamins, hydrophilic screening agents, urea, allantoin.

As other additives, there may also be mentioned fillers, water-soluble preservatives such as diazolidinylurea (Germal) or methyl parahydroxybenzoate (paraben), perfumes and neutralizing agents such as triethanolamine or sodium hydroxide for the purpose of adjusting the pH.

Thus, the gel according to the invention preferably comprises, by weight:

from 0.02% to 50% of organopolysiloxane solubilized in the aqueous phase, from 0.01% to 30% of hydrophilic polymer, from 0.001% to 10% of colouring material, from 0% to 30% of water-soluble or dispersible additive, and water q.s. 100%.

The subject of the invention is also a process for making up a human face, which consists of applying to the face a gel as defined above.

The gel of the invention is especially well suited to the production of a blusher, an eyeshadow or a make-up foundation.

Thus, further subjects of the invention are a blusher, an eyeshadow and a make-up foundation, consisting of an aqueous gel as defined above.

Other advantages and features will become more clearly apparent in the examples which follow, given by way of illustration and without implied limitation. The amounts are given as percentages by weight.

The gels illustrated below are stable over time.

EXAMPLE 1

Dark, Plum-coloured Blusher

| | |
|---|---|
| Carbopol 954 | 1.5% |
| Triethanolamine | 1.5% |
| Silivax WD-IS (*) | 5% |
| Polyvinylpyrrolidone | 1% |
| Polyethylene glycol 600 | 8.4% |
| Ponceau SX disodium salt | 0.18% |
| Alizarin green G disodium salt | 0.02% |
| Methyl para-hydroxybenzoate | q.s. |
| Water | q.s. 100% |

(*) oxyethylenated PDMS containing stearate groups, sold by the company Siltech.

This blusher was prepared at room temperature by mixing these constituents using a stirrer of the Rayneri turbo-mixer type.

This gel was easy to apply and imparted, after being spread on the skin, a very natural homogeneous makeup and an appearance of particularly good health. In addition, it displayed good staying power over time.

EXAMPLE 2

Caramel-coloured Make-up Foundation

| | |
|---|---|
| Carbopol 954 | 0.75% |
| Triethanolamine | 0.8% |
| Silicone emulsion TP 503 (*) | 14.28% |
| Ponceau SX disodium salt | 0.18% |
| Quinoline yellow | 0.14% |
| Alizarin green disodium salt | 0.08% |
| Methyl para-hydroxybenzoate | q.s. |
| Water | q.s. 100% |

(*) TP 503 sold by the company Union Carbide: Mixture of high molecular weight PDMS and cyclomethicones in emulsion in water; the emulsion displays particles in the region of 1 μm in diameter.

This make-up foundation was prepared under the same conditions as those of the previous example. A very soft gel was obtained, which did not become fluffy, was very cool on application and formed a film. It was applied homogeneously and endowed the skin with a slight natural tan.

EXAMPLE 3

Caramel-coloured Make-up Foundation

| | |
|---|---|
| Carbopol 954 | 1.5% |
| Triethanolamine | 2.5% |
| Silicone Non P protein (*) | 10% |
| Ponceau SX disodium salt | 0.18% |
| Alizarin green disodium salt | 0.08% |
| Quinoline yellow | 0.14% |
| Methyl para-hydroxybenzoate | q.s. |
| Water | q.s. 100% |

(*) copolymer of silicone with the grafting of a wheat protein, in water at a concentration of 35%, sold by the company Siltech.

This make-up foundation was prepared as in Example 1. A make-up was obtained which endowed the skin with an appearance of particularly good health, was easy to apply and had good staying power.

What is claimed is:

1. A make-up gel comprising an aqueous phase, a hydrophilic polymer as a gelling agent, and a colouring material which is soluble or dispersible in the aqueous phase, and further comprising at least one organopolysiloxane solubilized in the aqueous phase, wherein said at least one organopolysiloxane solubilized in the aqueous phase is selected from dimethicone copolyols and their derivatives and organopolysiloxanes solubilized using a surfactant of HLB (hydrophilic-lipophilic balance) value above 8.

2. A gel according to claim 1, wherein said at least one organopolysiloxane solubilized in the aqueous phase is present in an amount of 0.02–50% by weight relative to the total weight of the gel.

3. A gel according to claim 2, wherein said at least one organopolysiloxane solubilized in the aqueous phase is present in an amount of greater than 10% to 50% by weight relative to the total weight of the gel.

4. A gel according to claim 1, wherein said gel has an absolute viscosity of 0.1–10 Pa.s (1–100 poises) at 25° C.

5. A gel according to claim 4, wherein said gel has an absolute viscosity of 0.5–3 Pa.s (5–30 poises) at 25° C.

6. A gel according to claim 1, wherein said gel comprises, by weight relative to the total weight of the gel, 0.5–20% of dimethicone copolyol or a derivative thereof.

7. A gel according to claim 1, wherein said dimethicone copolyol derivatives are selected from dimethicone copolyols containing a phosphate, sulphate, myristamidopropyldimethylammonium chloride, stearate, amine-modified group, and glyco-modified group.

8. A gel according to claim 1, wherein said gel comprises, by weight relative to the total weight of the gel, 0.02–20% of an organopolysiloxane solubilized with said surfactant.

9. A gel according to claim 1, wherein the organopolysiloxane solubilized with said surfactant is selected from polydimethylsiloxanes and mixtures of polydimethylsiloxanes and cyclomethicones.

10. A gel according to claim 1, wherein the organopolysiloxane solubilized with a surfactant takes the form of a microemulsion, the average size of the particles of organopolysiloxane being on the order of 1 μm.

11. A gel according to claim 1, wherein said gel comprises, by weight relative to the total weight of the gel, 0.01–30% of said hydrophilic polymer.

12. A gel according to claim 1, wherein said hydrophilic polymer is selected from acrylic, polymethacrylic and/or carboxyvinyl polymers or copolymers; polysaccharide derivatives, xanthan, gellan and rhamsan polymers, alginates, maltodextrin, starch and its derivatives, hyaluronic acid and its salts, gum karaya, carob flour and guar derivatives; polyethylene glycols and their derivatives; and polyvinylpyrrolidones and their derivatives.

13. A gel according to claim 1, wherein said gel comprises, by weight relative to the total weight of the gel, 0.001–10% of said colouring material.

14. A gel according to claim 1, wherein said colouring material is selected from organic colorants and pigments, which are hydrophilic or rendered hydrophilic.

15. A gel according to claim 1, wherein said gel comprises, by weight relative to the total weight of the gel, 0 to 30% of a water-soluble or water-dispersible additive.

16. A gel according to claim 15, wherein the additive is a gelling agent selected from a hydrophilic silica or silicate, water-soluble active agents, neutralizing agents, water-soluble preservatives, perfumes, fillers and mixtures thereof.

17. A make-up foundation, comprising a gel according to claim 1.

18. A blusher or eyeshadow, comprising a gel according to claim 1.

19. A process for making up the human face, comprising the step of applying to the face a gel as defined in claim 1.

* * * * *